(12) United States Patent
Uehara

(10) Patent No.: US 7,887,787 B2
(45) Date of Patent: Feb. 15, 2011

(54) HAIR CONDITIONING COMPOSITION COMPRISING PRE-MIXTURE OF THREE KINDS OF SILICONES

(75) Inventor: Nobuaki Uehara, Kobe (JP)

(73) Assignee: The Procter & Gamble, Cincinnati, OH (US)

( * ) Notice: Subject to any disclaimer, the term of this patent is extended or adjusted under 35 U.S.C. 154(b) by 1211 days.

(21) Appl. No.: 11/055,872

(22) Filed: Feb. 11, 2005

(65) Prior Publication Data

US 2005/0180943 A1 Aug. 18, 2005

Related U.S. Application Data

(60) Provisional application No. 60/544,935, filed on Feb. 13, 2004.

(51) Int. Cl.
*A61Q 5/12* (2006.01)
(52) U.S. Cl. .................................................. 424/70.12
(58) Field of Classification Search ........................ None
See application file for complete search history.

(56) References Cited

U.S. PATENT DOCUMENTS 6,048,519 A * 4/2000 Hiraishi et al. ......... 424/70.122

FOREIGN PATENT DOCUMENTS

JP 06080538 A 9/1992
WO 99/34768 A2 7/1999

* cited by examiner

*Primary Examiner*—Jyothsna A Venkat
(74) *Attorney, Agent, or Firm*—Linda M. Sivik

(57) ABSTRACT

Disclosed is a hair conditioning composition comprising a silicone system comprising three types of silicones, and a gel matrix, wherein the silicone system comprising a first silicone having a high viscosity, a second silicone having a low viscosity, and a third silicone which is an aminosilicone, and wherein the composition is prepared by the steps of: the three types of silicones are mixed to form the silicone system; and the silicone system is mixed with the gel matrix. The composition of the present invention can provide improved conditioning benefits such as smooth feel and reduced friction.

1 Claim, No Drawings

HAIR CONDITIONING COMPOSITION COMPRISING PRE-MIXTURE OF THREE KINDS OF SILICONES

CROSS REFERENCE TO RELATED APPLICATION

This application claims the benefit of U.S. Provisional Application No. 60/544,935, filed Feb. 13, 2004.

FIELD OF THE INVENTION

The present invention relates to a hair conditioning composition comprising a silicone system comprising three types of silicones, and a gel matrix, and wherein the composition is prepared by the steps of: the three types of silicones are mixed to form the silicone system; and the silicone system is mixed with the gel matrix. The composition of the present invention can provide improved conditioning benefits such as smooth feel and reduced friction.

BACKGROUND OF THE INVENTION

Human hair becomes soiled due to its contact with the surrounding environment and from the sebum secreted by the scalp. The soiling of hair causes it to have a dirty feel and an unattractive appearance. The soiling of the hair necessitates shampooing with frequent regularity.

Shampooing cleans the hair by removing excess soil and sebum. However, shampooing can leave the hair in a wet, tangled, and generally unmanageable state. Once the hair dries, it is often left in a dry, rough, lusterless, or frizzy condition due to removal of the hair's natural oils and other natural conditioning and moisturizing components. The hair can further be left with increased levels of static upon drying, which can interfere with combing and result in a condition commonly referred to as "fly-away hair", or contribute to an undesirable phenomena of "split ends", particularly for long hair.

A variety of approaches have been developed to condition the hair. A common method of providing conditioning benefit to the hair is through the use of hair conditioning agents such as cationic surfactants and polymers, high melting point fatty compounds, low melting point oils, silicone compounds, and mixtures thereof. Most of these conditioning agents are known to provide conditioning benefits by depositing on the hair. For example, silicone compounds are known to provide conditioning benefits such as smooth feel to the hair, by depositing on the hair.

Japanese Patent Laid-open H6-80538 discloses hair cosmetics comprising a high molecular weight silicone, a low molecular weight silicone, a silicone compound containing nitrogen atoms, a liquid crystal forming nonionic amphiphilic compound, and alcohols and/or esters, expecting that the composition provides smooth feel, flexibility, dry feeling, and moist feeling to the hair.

It has been found that; it is still not easy to obtain expected conditioning efficacy, especially conditioning benefits such as smooth feel and reduced friction on dry hair by the composition of Japanese Patent Laid-open H6-80538. It has been also found that; it is still not easy to obtain the above conditioning benefits especially on damaged hair by the composition of Japanese Patent Laid-open H6-80538. Human hair becomes damaged due to, for example, shampooing, combing, permanent waves, and/or coloring the hair. Such damaged hair is often left hydrophilic and/or in a rough condition especially when the hair dries, compared to non-damaged or less damaged hair. There is a need for hair conditioning compositions which provide improved conditioning benefits such as smooth feel and reduced friction on dry hair, especially on damaged hair.

Based on the foregoing, there remains a desire for hair conditioning compositions which provide improved conditioning benefits such as smooth feel and reduced friction on dry hair, especially on damaged hair.

There also exists a desire for hair conditioning compositions which provide the above conditioning benefits, while providing other conditioning benefits such as slippery feel and slick feel on wet hair.

None of the existing art provides all of the advantages and benefits of the present invention.

SUMMARY OF THE INVENTION

The present invention is directed to a hair conditioning composition comprising by weight:
(a) from about 0.1% to about 20% of a silicone system comprising:
  (i) a first silicone which is non-volatile, substantially free of amino groups, and has a viscosity of from about 100,000 mm$^2 \cdot$s$^{-1}$ to about 30,000,000 mm$^2 \cdot$s$^{-1}$;
  (ii) a second silicone which is non-volatile, substantially free of amino groups, and has a viscosity of from about 5 mm$^2 \cdot$s$^{-1}$ to about 10,000 mm$^2 \cdot$s$^{-1}$; and
  (iii) a third silicone which is an aminosilicone having a viscosity of from about 100 mm$^2 \cdot$s$^{-1}$ to about 50,000 mm$^2 \cdot$s$^{-1}$;
(b) a gel matrix comprising:
  (i) from about 0.1% to about 10% of an cationic surfactant having the following general formula;

(I)

wherein one of $R^{71}$, $R^{72}$, $R^{73}$ and $R^{74}$ is selected from an aliphatic group of from 16 to 30 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$ and $R^{74}$ are independently selected from an aliphatic group of from 1 to about 8 carbon atoms or an aromatic, alkoxy, polyoxyalkylene, alkylamido, hydroxyalkyl, aryl or alkylaryl group having up to about 8 carbon atoms; and X$^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals;
  (ii) from about 0.1% to about 20% of a high melting point fatty compound; and
  (iii) an aqueous carrier;

wherein the composition is prepared by a method comprising the steps of:
(a) mixing the first, second, and third silicones to form the silicone system; and
(b) mixing the silicone system with the gel matrix.

The hair conditioning composition of the present invention can provide improved conditioning benefits such as smooth feel and reduced friction. These and other features, aspects, and advantages of the present invention will become better understood from a reading of the following description, and appended claims.

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

Compositions

The composition comprises the silicone system and the gel matrix, and is prepared by a method comprising the steps of:
(a) mixing the first, second, and third silicones to form the silicone system; and
(b) mixing the silicone system with the gel matrix.

The addition of the silicone system, i.e., the addition of the first, the second, and the third silicones in the form of a pre-mixture, provides improved conditioning benefits such as smooth feel and reduced friction. It has been found that the addition of the silicones in the form of the pre-mixture can provide improved deposition of the silicones.

Damaged hair is less hydrophobic compared to non-damaged and/or less damaged hair. It is believed that, by providing improved hydrophobicity to hair, the hair conditioning composition can provide improved smooth feel and reduced friction to the hair. It is also believed that, the improved hydrophobicity to the hair can be provided by, for example, improved deposition of the silicones due to the above premixture. It is also believed that the improved hydrophobicity to the hair can be provided by some other preferred features of the present invention, for example, the use of preferred first silicone, second silicone, third silicone, and/or cationic surfactants. Further, without being limited to the theory, it is believed that improved hydrophobicity provides improved tolerance to the hair for humidity in the surrounded circumstance, thus provides reduced frizziness and/or fly-away in rainy day and/or humid day.

The hair conditioning composition of the present invention is preferably substantially free of anionic compounds. Anionic compounds herein include anionic surfactants and anionic polymers. In the present invention, "substantially free of anionic compounds" means that the composition contain 1% or less, preferably 0.5% or less, more preferably 0% of anionic compounds.

The hair conditioning composition of the present invention has a pH of preferably from about 3 to about 9, more preferably from about 3 to about 7.

Silicone System

The hair conditioning composition of the present invention comprises a silicone system comprising following 3 silicone compounds: (i) a first silicone which is non-volatile, substantially free of amino groups, and has a viscosity of from about 100,000 $mm^2 \cdot s^{-1}$ to about 30,000,000 $mm^2 \cdot s^{-1}$; (ii) a second silicone which is non-volatile, substantially free of amino groups, and has a viscosity of from about 5 $mm^2 \cdot s^{-1}$ to about 10,000 $mm^2 \cdot s^{-1}$; and (iii) a third silicone which is an aminosilicone having a viscosity of from about 100 $mm^2 \cdot s^{-1}$ to about 50,000 $mm^2 \cdot s^{-1}$.

The silicone system is prepared by mixing the first, the second, and the third silicones. The silicone system can be prepared by, for example, either of following method (i) to (iii):
(i) Mixing the first, second and third silicone concurrently;
(ii) Mixing the first and the second silicones, and then mixing the third silicone with them; and
(iii) Mixing the second and the third silicones, and then mixing the first silicone with them.

When preparing the silicone system, the first, the second, and the third silicones are mixed with stirring until they are homogenized to form the silicone system.

The viscosity can be measured by means of, for example, a glass capillary viscometer as set forth in Dow Corning Corporate Test Method CTM0004, Jul. 20, 1970, which is incorporated by reference herein in its entirety.

The silicone system is contained in the composition of the present invention at a level by weight of from about 0.1% to about 20%, preferably from about 0.5% to about 15%, more preferably from about 1% to about 10%. Preferably, the silicone system has a viscosity of from about 500 $mm^2 \cdot s^{-1}$ to about 100,000 $mm^2 \cdot s^{-1}$, more preferably from about 1,000 $mm^2 \cdot s^{-1}$ to about 50,000 $mm^2 \cdot s^{-1}$, still more preferably from about 1,000 $mm^2 \cdot s^{-1}$ to about 30,000 $mm^2 \cdot s^{-1}$, even more preferably from about 1,000 $mm^2 \cdot s^{-1}$ to about 20,000 $mm^2 s^{-1}$, and highly preferably from about 1,000 $mm^2 \cdot s^{-1}$ to about 5,000 $mm^2 \cdot s^{-1}$.

Preferably, the first and the second silicones are contained at a level such that the weight ratio of the first silicone to the second silicone is preferably from about 1:1 to about 1:10, more preferably from about 1:1 to about 1:6.

Preferably, the first, the second, and the third silicones are contained at a level such that the weight ratio of the third silicone to the total of the first and the second silicones is from about 1:1 to about 1:50, more preferably from about 1:1 to about 1:20, still more preferably from about 1:1 to about 1:10.

First Silicone

The hair conditioning composition of the present invention comprises a first silicone. The first silicone is non-volatile, and substantially free of amino groups. In the present invention, the first silicone being "substantially free of amino groups" means that the first silicone contains 0% of amino groups. The first silicone has a viscosity of from about 100,000 $mm^2 \cdot s^{-1}$ to about 30,000,000 $mm^2 \cdot s^{-1}$ at 25° C., preferably from about 100,000 $mm^2 \cdot s^{-1}$ to about 20,000,000, more preferably from about 200,000 $mm^2 \cdot s^{-1}$ to about 800,000 $mm^2 \cdot s^{-1}$. The first silicone has a molecular weight of preferably from about 100,000 to about 1,000,000, more preferably from about 100,000 to about 600,000, still more preferably from about 120,000 to about 300,000. The first silicone compound is preferably nonionic.

The first silicone compound is contained in the composition at a level by weight of, preferably from about 0.1% to about 10%, more preferably from about 0.1% to about 5%, still more preferably from about 0.1% to about 2%.

Preferred first non-volatile silicone compounds useful herein include polyalkyl or polyaryl siloxanes with the following structure:

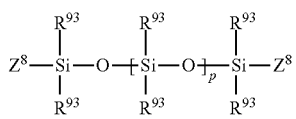

wherein $R^{93}$ is alkyl or aryl, and p is an integer from about 1,300 to about 15,000, more preferably from about 1,600 to about 8,000, still more preferably from about 1,600 to about 4,000. $Z^8$ represents groups which block the ends of the silicone chains. The alkyl or aryl groups substituted on the siloxane chain ($R^{93}$) or at the ends of the siloxane chains $Z^8$ can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable $Z^8$ groups include hydroxy, methyl, methoxy, ethoxy, propoxy, and aryloxy. The two $R^{93}$ groups on the silicon atom may represent the same group or different groups. Preferably, the two $R^{93}$ groups represent the same group. Suitable $R^{93}$ groups include methyl, ethyl, propyl, phenyl, methylphenyl and phenylmethyl. The preferred silicone compounds are polydimethylsiloxane, polydiethylsiloxane, and polymethylphenylsiloxane. Polydimethylsiloxane, which is also known as dimethicone, is especially preferred. Commercially available these silicone compounds useful herein include, for example, those available from the General Electric Company in their TSF451 series, and those available from Dow Corning in their Dow Corning SH200 series.

The silicone compounds that can be used herein also include a silicone gum. The term "silicone gum", as used herein, means a polyorganosiloxane material having a viscosity at 25° C. of greater than or equal to 1,000,000 mm²·s⁻¹. It is recognized that the silicone gums described herein can also have some overlap with the above-disclosed silicone compounds. This overlap is not intended as a limitation on any of these materials. The "silicone gums" will typically have a mass molecular weight in excess of about 165,000, generally between about 165,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. Commercially available silicone gums useful herein include, for example, TSE200A available from the General Electric Company.

Second Silicone

The hair conditioning composition of the present invention comprises a second silicone. The second silicone is non-volatile, and substantially free of amino groups. In the present invention, the second silicone being "substantially free of amino groups" means that the second silicone contains 0% of amino groups. The second silicone has a viscosity of from about 5 mm²·s⁻¹ to about 10,000 mm²·s⁻¹ at 25° C., preferably from about 5 mm²·s⁻¹ to about 5,000 mm²·s⁻¹, more preferably from about 10 mm²·s⁻¹ to about 1,000 mm²·s⁻¹, still more preferably from about 20 mm²·s⁻¹ to about 350 mm²·s⁻¹. The second silicone has a molecular weight of preferably from about 400 to about 65,000, more preferably from about 800 to about 50,000, still more preferably from about 400 to about 30,000, even more preferably from about 400, to about 15,000. The second silicone is preferably nonionic. The second silicone is preferably a linear silicone.

The second silicone is contained in the composition at a level by weight of, preferably from about 0.1% to about 17%, more preferably from about 0.4% to about 10%, still more preferably from about 1% to about 5%.

Preferred second non-volatile silicone compounds useful herein include polyalkyl or polyaryl siloxanes with the following structure:

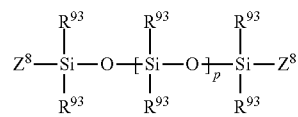

wherein $R^{93}$ is alkyl or aryl, and p is an integer from about 7 to about 850, more preferably from about 7 to about 665, still more preferably from about 7 to about 400, even more preferred from about 7 to about 200. $Z^8$ represents groups which block the ends of the silicone chains. The alkyl or aryl groups substituted on the siloxane chain ($R^{93}$) or at the ends of the siloxane chains $Z^8$ can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable $Z^8$ groups include hydroxy, methyl, methoxy, ethoxy, propoxy, and aryloxy. The two $R^{93}$ groups on the silicon atom may represent the same group or different groups. Preferably, the two $R^{93}$ groups represent the same group. Suitable $R^{93}$ groups include methyl, ethyl, propyl, phenyl, methylphenyl and phenylmethyl. The preferred silicone compounds are polydimethylsiloxane, polydiethylsiloxane, and polymethylphenylsiloxane. Polydimethylsiloxane, which is also known as dimethicone, is especially preferred. Commercially available these silicone compounds useful herein include, for example, those available from the General Electric Company in their TSF451 series, and those available from Dow Corning in their Dow Corning SH200 series.

Third Silicone

The hair conditioning composition of the present invention comprises a third silicone which is an aminosilicone. It is believed that; the aminosilicones can provide improved deposition of overall silicones, especially on damaged hair. The aminosilicones useful herein are those having a viscosity of from about 100 mm²·s⁻¹ to about 50,000 mm²·s⁻¹, preferably from about 1,000 mm²·s⁻¹ to about 25,000 mm²·s⁻¹, more preferably from about 1,000 mm²·s⁻¹ to about 8,000 mm²·s⁻¹, at 25° C. The aminosilicones useful herein are those having a molecular weight of preferably from about 6,000 to about 110,000, and having a nitrogen content by weight of preferably from about 0.1% to about 0.8%, more preferably from about 0.1% to about 0.5%, still more preferably from about 0.1% to about 0.25%.

The aminosilicone is contained in the composition at a level by weight of, preferably from about 0.1% to about 10%, more preferably from about 0.1% to about 5%, still more preferably from about 0.1% to about 1%.

Preferred aminosilicones useful herein include alkylamino substituted silicone compounds having the following structure:

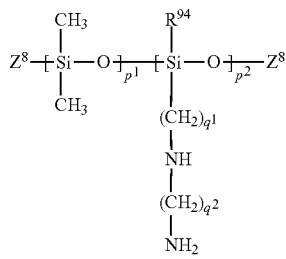

wherein $R^{94}$ is H, $CH_3$, OH, or alkoxy having from 1 to 3 carbon atoms, preferably $CH_3$; $p^1$ is an integer of 1 or above, preferably from about 10 to about 1,300, more preferably from about 100 to about 1,000; $p^2$ is an integer of 1 or above, preferably from 1 to about 10; wherein sum of $p^1$ and $p^2$ is from 2 to about 1,500, preferably from about 100 to 1,000; and $q^1$ and $q^2$ are independently integers of from 1 to about 10, preferably from 1 to about 5, more preferably $q^1$ is an integer of 3 and $q^2$ is an integer of 2. $Z^8$ represents groups which block the ends of the silicone chains. $Z^8$ groups useful herein include, for example, hydroxy, methyl, alkoxy, and aryloxy, wherein the alkoxy and aryloxy groups are those independently having from 1 to about 20 carbon atoms, preferably from 1 to 3 carbon atoms. Preferably, $Z^8$ groups are independently hydroxy or alkoxy having from 1 to 3 carbon atoms. More preferably, at least one $Z^8$ group is the alkoxy having from 1 to 3 carbon atoms. Still more preferably, at least one $Z^8$ group is methoxy. Commercially available aminosilicones having the above formula include, for example, ADM1100 available from Wacker and DC2-8040 available from Dow Corning.

Highly preferred aminosilicones are those having the above structure wherein $R^{94}$ is $CH_3$; $p^1$ is an integer of from about 100 to about 1,000; $p^2$ is an integer of from about 1 to about 10; wherein sum of $p^1$ and $p^2$ is from 100 to 1,000; $q^1$ is an integer of 3 and $q^2$ is an integer of 2; and $Z^8$ groups are independently hydroxy or alkoxy having from 1 to 3 carbon atoms. Commercially available highly preferred aminosilicones includes, for example, ADM1100 available from Wacker. It is believed that; the highly preferred aminosilicones can provide improved hydrophobicity and reduced friction to the hair, compared to other aminosilicones.

Another preferred aminosilicones useful herein include those known as "amodimethicone". Commercially available amodimethicones useful herein include, for example, BY16-872 available from Dow Corning.

Gel Matrix

The composition of the present invention comprises a gel matrix comprising a cationic surfactant, a high melting fatty compound, and an aqueous carrier. The cationic surfactant, together with the high melting fatty compound, and an aqueous carrier, provides a gel matrix which is suitable for providing various conditioning benefits, especially slippery and slick feel on wet hair. In view of providing the above gel matrix, the cationic surfactant and the high melting point fatty compound are contained at a level such that the mole ratio of the cationic surfactant to the high melting point fatty compound is in the range of, preferably from about 1:1 to about 1:10, more preferably from about 1:2 to about 1:6, in view of providing the above conditioning benefits especially slippery and slick feel on wet hair.

Cationic Surfactant

The compositions of the present invention comprise a cationic surfactant. The cationic surfactant is a mono-long alkyl quaternized ammonium salt having the formula (I):

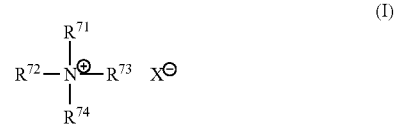

wherein one of $R^{71}$, $R^{72}$, $R^{73}$ and $R^{74}$ is selected from an aliphatic group of from 16 to 30 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$ and $R^{74}$ are independently selected from an aliphatic group of from 1 to about 8 carbon atoms or an aromatic, alkoxy, polyoxyalkylene, alkylamido, hydroxyalkyl, aryl or alkylaryl group having up to about 8 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Preferably, one of $R^{71}$, $R^{72}$, $R^{73}$ and $R^{74}$ is selected from an alkyl group of from 16 to 30 carbon atoms, more preferably from 18 to 26 carbon atoms, still more preferably from 22 carbon atoms; the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof; and X is selected from the group consisting of Cl, Br, $CH_3OSO_3$, and mixtures thereof. It is believed that such mono-long alkyl quaternized ammonium salts can provide improved slippery and slick feel on wet hair, compared to multi-long alkyl quaternized ammonium salts. It is also believed that mono-long alkyl quaternized ammonium salts can provide improved hydrophobicity and smooth feel on dry hair, compared to amine or amine salt cationic surfactants.

Nonlimiting examples of such mono-long alkyl quaternized ammonium salt cationic surfactants include: behenyl trimethyl ammonium chloride available, for example, with tradename Genamine KDMP from Clariant, with tradename INCROQUAT TMC-80 from Croda and ECONOL TM22 from Sanyo Kasei; stearyl trimethyl ammonium chloride available, for example, with tradename CA-2450 from Nikko Chemicals; cetyl trimethyl ammonium chloride available, for example, with tradename CA-2350 from Nikko Chemicals; hydrogenated tallow alkyl trimethyl ammonium chloride; stearyl dimethyl benzyl ammonium chloride; and stearoyl amidopropyl dimethyl benzyl ammonium chloride.

Among them, more preferred cationic surfactants are those having a longer alkyl group, i.e., C22 alkyl group. Such cationic surfactant includes, for example, behenyl trimethyl ammonium chloride. It is believed that; cationic surfactants having a longer alkyl group provide improved hydrophobicity on dry hair, compared to cationic surfactant having a shorter alkyl group. It is also believed that; compared to cationic surfactants having a shorter alkyl group, cationic surfactants having a long alkyl group can provide improved hydrophobicity to the hair, especially to damaged hair, when combined with the pre-mixture of the silicones of the present invention. Alternatively, it is believed that; cationic surfactant having an adequate length of alkyl group provides improved slippery and slick feel on wet hair, compared to a cationic surfactant having too long alkyl group. Thus, it is believed that the selection of C22 alkyl group among long alkyl groups provides balanced benefits between improved hydrophobicity on dry hair and improved slippery and slick feel on wet hair.

The cationic surfactant is included in the composition at a level by weight of preferably from about 0.1% to about 10%, more preferably from about 1% to about 8%, still more preferably from about 1.5% to about 5%.

High Melting Point Fatty Compound

The hair conditioning composition of the present invention comprises a high melting point fatty compound. The high melting point fatty compound useful herein have a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

The high melting point fatty compound can be included in the composition at a level of from about 0.1% to about 20%, preferably from about 1% to about 10%, still more preferably from about 2% to about 8%, by weight of the composition.

The fatty alcohols useful herein are those having from about 14 to about 30 carbon atoms, preferably from about 16 to about 22 carbon atoms. These fatty alcohols are saturated and can be straight or branched chain alcohols. Nonlimiting examples of fatty alcohols include, cetyl alcohol, stearyl alcohol, behenyl alcohol, and mixtures thereof.

The fatty acids useful herein are those having from about 10 to about 30 carbon atoms, preferably from about 12 to about 22 carbon atoms, and more preferably from about 16 to about 22 carbon atoms. These fatty acids are saturated and can be straight or branched chain acids. Also included are diacids, triacids, and other multiple acids which meet the requirements herein. Also included herein are salts of these fatty acids. Nonlimiting examples of fatty acids include lauric acid, palmitic acid, stearic acid, behenic acid, sebacic acid, and mixtures thereof.

The fatty alcohol derivatives and fatty acid derivatives useful herein include alkyl ethers of fatty alcohols, alkoxylated fatty alcohols, alkyl ethers of alkoxylated fatty alcohols, esters of fatty alcohols, fatty acid esters of compounds having esterifiable hydroxy groups, hydroxy-substituted fatty acids, and mixtures thereof. Nonlimiting examples of fatty alcohol derivatives and fatty acid derivatives include materials such as methyl stearyl ether; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; $C_1$-$C_{30}$ alkyl ethers of the ceteth, steareth, and ceteareth compounds just described; polyoxyethylene ethers of behenyl alcohol; ethyl stearate, cetyl stearate, cetyl palmitate, stearyl stearate, myristyl myristate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, glyceryl monostearate, glyceryl distearate, glyceryl tristearate, and mixtures thereof.

High melting point fatty compounds of a single compound of high purity are preferred. Single compounds of pure fatty alcohols selected from the group of pure cetyl alcohol, stearyl alcohol, and behenyl alcohol are highly preferred. By "pure" herein, what is meant is that the compound has a purity of at least about 90%, preferably at least about 95%. These single compounds of high purity provide good rinsability from the hair when the consumer rinses off the composition.

Commercially available high melting point fatty compounds useful herein include: cetyl alcohol, stearyl alcohol, and behenyl alcohol having tradenames KONOL series available from Shin Nihon Rika (Osaka, Japan), and NAA series available from NOF (Tokyo, Japan); pure behenyl alcohol having tradename 1-DOCOSANOL available from WAKO (Osaka, Japan), various fatty acids having tradenames NEO-FAT available from Akzo (Chicago Ill., USA), HYSTRENE available from Witco Corp. (Dublin Ohio, USA), and DERMA available from Vevy (Genova, Italy).

Aqueous Carrier

The hair conditioning composition of the present invention comprises an aqueous carrier. The level and species of the carrier are selected according to the compatibility with other components, and other desired characteristic of the product.

The carrier useful in the present invention includes water and water solutions of lower alkyl alcohols and polyhydric alcohols. The lower alkyl alcohols useful herein are monohydric alcohols having 1 to 6 carbons, more preferably ethanol and isopropanol. The polyhydric alcohols useful herein include propylene glycol, hexylene glycol, glycerin, and propane diol.

Preferably, the aqueous carrier is substantially water. Deionized water is preferably used. Water from natural sources including mineral cations can also be used, depending on the desired characteristic of the product. Generally, the compositions of the present invention comprise from about 20% to about 95%, preferably from about 30% to about 92%, and more preferably from about 50% to about 90% water.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: other conditioning agents such as hydrolysed collagen with tradename Peptein 2000 available from Hormel, vitamin E with tradename Emix-d available from Eisai, panthenol available from Roche, panthenyl ethyl ether available from Roche, hydrolysed keratin, proteins, plant extracts, and nutrients; emollients such as PPG-3 myristyl ether with tradename Varonic APM available from Goldschmidt, Trimethyl pentanol hydroxyethyl ether, PPG-11 stearyl ether with tradename Varonic APS available from Goldschmidt, Stearyl heptanoate with tradename Tegosoft SH available from Goldschmidt, Lactil (mixture of Sodium lactate, Sodium PCA, Glycine, Fructose, Urea, Niacinamide, Inositol, Sodium Benzoate, and Lactic acid) available from Goldschmidt, Ethyl hexyl palmitate with tradename Saracos available from Nishin Seiyu and with tradename Tegosoft OP available from Goldschmidt; hair-fixative polymers such as amphoteric fixative polymers, cationic fixative polymers, anionic fixative polymers, nonionic fixative polymers, and silicone grafted copolymers; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; hair oxidizing (bleaching) agents, such as hydrogen peroxide, perborate and persulfate salts; hair reducing agents such as the thioglycolates; perfumes; and sequestering agents, such as disodium ethylenediamine tetra-acetate; ultraviolet and infrared screening and absorbing agents such as octyl salicylate; and antidandruff agents such as zinc pyrithione and salicylic acid.

Polysorbate

The hair conditioning composition of the present invention may contain a polysorbate, in view of adjusting rheology. Preferred polysorbate useful herein includes, for example, polysorbate-20, polysorbate-21, polysorbate-40, polysorbate-60, and mixtures thereof. Highly preferred is polysorbate-20.

The polysorbate can be contained in the composition at a level by weight of preferably from about 0.01% to about 5%, more preferably from about 0.05% to about 2%.

Polypropylene Glycol

Polypropylene glycol useful herein are those having a weight average molecular weight of from about 200 g/mol to about 100,000 g/mol, preferably from about 1,000 g/mol to about 60,000 g/mol. Without intending to be limited by theory, it is believed that the polypropylene glycol herein deposits onto, or is absorbed into hair to act as a moisturizer buffer, and/or provides one or more other desirable hair conditioning benefits.

The polypropylene glycol useful herein may be either water-soluble, water-insoluble, or may have a limited solubility in water, depending upon the degree of polymerization and whether other moieties are attached thereto. The desired solubility of the polypropylene glycol in water will depend in large part upon the form (e.g., leave-on, or rinse-off form) of the hair care composition. For example, a rinse-off hair care composition, it is preferred that the polypropylene glycol herein has a solubility in water at 25° C. of less than about 1 g/100 g water, more preferably a solubility in water of less than about 0.5 g/100 g water, and even more preferably a solubility in water of less than about 0.1 g/100 g water.

The polypropylene glycol can be included in the hair conditioning composition of the present invention at a level of, preferably from about 0.01% to about 10%, more preferably from about 0.05% to about 6%, still more preferably from about 0.1% to about 3% by weight of the composition.

Low Melting Point Oil

Low melting point oils useful herein are those having a melting point of less than 25° C. The low melting point oil useful herein is selected from the group consisting of: hydrocarbon having from 10 to about 40 carbon atoms; unsaturated fatty alcohols having from about 10 to about 30 carbon atoms such as oleyl alcohol; unsaturated fatty acids having from about 10 to about 30 carbon atoms; fatty acid derivatives; fatty alcohol derivatives; ester oils such as pentaerythritol ester oils, trimethylol ester oils, citrate ester oils, and glyceryl ester oils; poly α-olefin oils; and mixtures thereof. Preferred low melting point oils herein are selected from the group consisting of: ester oils such as pentaerythritol ester oils, trimethylol ester oils, citrate ester oils, and glyceryl ester oils; poly α-olefin oils; and mixtures thereof, Particularly useful pentaerythritol ester oils and trimethylol ester oils herein include pentaerythritol tetraisostearate, pentaerythritol tetraoleate, trimethylolpropane triisostearate, trimethylolpropane trioleate, and mixtures thereof. Such compounds are available from Kokyo Alcohol with tradenames KAKPTI, KAKTTI, and Shin-nihon Rika with tradenames PTO, ENUJERUBU TP3SO.

Particularly useful citrate ester oils herein include triisocetyl citrate with tradename CITMOL 316 available from Bemel, triisostearyl citrate with tradename PELEMOL TISC available from Phoenix, and trioctyldodecyl citrate with tradename CITMOL 320 available from Bernel.

Particularly useful glyceryl ester oils herein include triisostearin with tradename SUN ESPOL G-318 available from Taiyo Kagaku, triolein with tradename CITHROL GTO available from Croda Surfactants Ltd., trilinolein with tradename EFADERMA-F available from Vevy, or tradename EFA-GLYCERIDES from Brooks.

Particularly useful poly α-olefin oils herein include polydecenes with tradenames PURESYN 6 having a number average molecular weight of about 500 and PURESYN 100 having a number average molecular weight of about 3000 and PURESYN 300 having a number average molecular weight of about 6000 available from Exxon Mobil Co.

Cationic Polymer

Cationic polymers useful herein are those having an average molecular weight of at least about 5,000, typically from about 10,000 to about 10 million, preferably from about 100,000 to about 2 million.

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. Other suitable spacer monomers include vinyl esters, vinyl alcohol (made by hydrolysis of polyvinyl acetate), maleic anhydride, propylene glycol, and ethylene glycol. Other suitable cationic polymers useful herein include, for example, cationic celluloses, cationic starches, and cationic guar gums.

Polyethylene Glycol

Polyethylene glycol can also be used as an additional component. The polyethylene glycols useful herein that are especially preferred are PEG-2M wherein n has an average value of about 2,000 (PEG-2M is also known as Polyox WSR® N-10 from Union Carbide and as PEG-2,000); PEG-5M wherein n has an average value of about 5,000 (PEG-5M is also known as Polyox WSR® N-35 and as Polyox WSR® N-80, both from Union Carbide and as PEG-5,000 and Polyethylene Glycol 300,000); PEG-7M wherein n has an average value of about 7,000 (PEG-7M is also known as Polyox WSR® N-750 from Union Carbide); PEG-9M wherein n has an average value of about 9,000 (PEG-9M is also known as Polyox WSR® N-3333 from Union Carbide); and PEG-14M wherein n has an average value of about 14,000 (PEG-14M is also known as Polyox WSR® N-3000 from Union Carbide).

Product Forms

The hair conditioning compositions of the present invention can be in the form of rinse-off products or leave-on products, can be opaque, and can be formulated in a wide variety of product forms, including but not limited to creams, gels, emulsions, mousses and sprays.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

The compositions of the present invention are suitable for rinse-off products and leave-on products, and are particularly useful for making products in the form of emulsion, cream, gel, spray or, mousse.

| Components | Compositions (wt %) | | | | | | |
|---|---|---|---|---|---|---|---|
| | Ex. 1 | Ex. 2 | Ex. 3 | Ex. 4 | Ex. 5 | Ex. 6 | Ex. 7 |
| First silicone-1 *1 | 0.63 | 0.63 | — | 0.63 | 0.63 | — | 1.34 |
| First silicone-2 *2 | — | — | 0.63 | — | — | 0.63 | — |
| Second silicone-1 *3 | 3.57 | 3.57 | — | 3.57 | 3.57 | 3.57 | 2.86 |
| Second silicone-2 *4 | — | — | 3.57 | — | — | — | — |
| Third silicone-1 *5 | 0.5 | 0.5 | 0.5 | — | — | 0.5 | 1.0 |
| Third silicone-2 *6 | — | — | — | 0.5 | — | — | — |
| Third silicone-3 *7 | — | — | — | — | 0.5 | — | — |
| Behenyl trimethyl ammonium chloride *8 | 3.38 | 2.25 | 3.38 | 2.25 | 3.38 | 2.25 | 3.38 |
| Isopropyl alcohol *8 | 0.899 | 0.598 | 0.899 | 0.598 | 0.899 | 0.598 | 0.899 |
| Cetyl alcohol *9 | 2.3 | 1.9 | 2.3 | 1.9 | 2.3 | 1.9 | 2.3 |
| Stearyl alcohol *10 | 4.2 | 4.6 | 4.2 | 4.6 | 4.2 | 4.6 | 4.2 |
| Polysorbate-20 *11 | — | — | — | — | 0.2 | — | — |
| PPG-34 *12 | — | — | — | — | — | — | 0.5 |
| Poly-α-olefin oil *13 | — | — | — | 0.5 | — | — | — |
| Benzyl alcohol | 0.4 | 0.4 | 0.4 | 0.4 | 0.4 | 0.4 | 0.4 |
| Methylchloroisothiazolinone/ Methylisothiazolinone | 0.0005 | 0.0005 | 0.0005 | 0.0005 | 0.0005 | 0.0005 | 0.0005 |
| Perfume | 0.5 | 0.5 | 0.5 | 0.5 | 0.5 | 0.5 | 0.5 |
| NaOH | 0.014 | 0.014 | 0.014 | 0.014 | 0.014 | 0.014 | 0.014 |
| Panthenol *15 | 0.05 | 0.05 | 0.05 | 0.05 | — | 0.05 | 0.05 |
| Panthenyl ethyl ether *16 | 0.05 | 0.05 | 0.05 | 0.05 | — | 0.05 | 0.05 |
| Hydrolyzed collagen *17 | — | — | 0.01 | 0.01 | 0.01 | — | 0.01 |
| Vitamin E *18 | — | — | 0.01 | 0.01 | 0.01 | — | 0.01 |
| Octyl methoxycinnamate | — | — | 0.09 | 0.09 | 0.09 | — | 0.09 |
| Benzophenone-3 | — | — | 0.09 | 0.09 | 0.09 | — | 0.09 |
| Disoudium EDTA | 0.1 | 0.1 | 0.1 | 0.1 | 0.1 | 0.1 | 0.1 |
| Deionized Water | q.s. to 100% | | | | | | |

Definitions of Components

*1 First silicone compound-1: dimethylpolysiloxane having a viscosity of 500,000 mm$^2$ · s$^{-1}$, available from GE Toshiba
*2 First silicone compound-2: dimethylpolysiloxane having a viscosity of 18,000,000 mm$^2$ · s$^{-1}$, available from GE Toshiba
*3 Second silicone compound-1: dimethylpolysiloxane having a viscosity of 200 mm$^2$ · s$^{-1}$, available from GE Toshiba
*4 Second silicone compound-2: dimethylpolysiloxane having a viscosity of 20 mm$^2$ · s$^{-1}$, available from GE Toshiba
*5 Third silicone compound-1: Available from Wacker with a tradename AD1100 and having a viscosity of 4,000 mm$^2$ · s$^{-1}$.
*6 Third silicone compound-2: Available from Dow Corning with a tradename DC2-8040 and having a viscosity of 3,000 mm$^2$ · s$^{-1}$.
*7 Third silicone compound-3: Amodimethicone having a viscosity of 20,000 mm$^2$ · s$^{-1}$, with a tradename BY16-872 available from Dow Corning.
*8 Behenyl trimethyl ammonium chloride/Isopropyl alcohol: Genamin KDMP available from Clariant
*9 Cetyl alcohol: Konol series available from Shin Nihon Rika.
*10 Stearyl alcohol: Konol series available from Shin Nihon Rika.
*11 Polysorbate-20: Glycosperse L-20K available from Lonza Inc.
*12 PPG-34: New Pol PP-2000 available from Sanyo Kasei.
*13 Poly-α-olefin oil: Puresyn 100 available from Exxon Mobil
*14 Methylchloroisothiazolinone/Methylisothiazolinone: Kathon CG available from Rohm & Haas
*15 Panthenol: Available from Roche.
*16 Panthenyl ethyl ether: Available from Roche.
*17 Hydrolyzed collagen: Peptein 2000 available from Hormel.
*18 Vitamin E: Emix-d available from Eisai.

Method of Preparation

The hair conditioning compositions of "Ex. 1" through "Ex. 7" as shown above can be prepared by any conventional method well known in the art. They are suitably made as follows:

Deionized water is heated to 85° C. Cationic surfactants and high melting point fatty compounds are mixed into the water. The water is maintained at a temperature of about 85° C. until the components are homogenized, and no solids are observed. The mixture is then cooled to about 55° C. and maintained at this temperature, to form a gel matrix. Separately, silicone system is prepared by mixing the first, second and third silicone compounds until they are homogenized. The silicone system is added to the gel matrix. When included, poly α-olefin oils, polypropylene glycols, and/or polysorbates are also added to the gel matrix. The gel matrix is maintained at about 50° C. during this time with constant stirring to assure homogenization. After it is homogenized, it is cooled to room temperature. When included, other additional components such as perfumes and preservatives are added with agitation. A triblender and/or mill can be used in each step, if necessary to disperse the materials.

The embodiments disclosed and represented by the previous "Ex. 1." through "Ex. 7" have many advantages. For example, they can provide improved conditioning benefits such as smooth feel and reduced friction to both damaged hair and non-damaged hair, while providing other benefits such as slippery and slick feel on wet hair.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair conditioning composition comprising by weight:
    (a) from about 1% to about 10% of a silicone system comprising:
        (i) a first silicone which is non-volatile, substantially free of amino groups, and has a viscosity of from about 300,000 $mm^2 \cdot s^{-1}$ to 700,000 $mm^2 \cdot s^{-1}$, wherein the first silicone is polydimethyl siloxane;
        (ii) a second silicone which is non-volatile, substantially free of amino groups, and has a viscosity of from about 30 $mm^2 \cdot s^{-1}$ to 100 $mm^2 \cdot s^{-1}$, wherein the first silicone is polydimethyl siloxane; and
        (iii) a third silicone which is an aminosilicone having a viscosity of from about 3,000 $mm^2 \cdot s^{-1}$ to 7,000 $mm^2 \cdot s^{-1}$; wherein the silicone system forms a silicone pre-mixture;
    (b) a gel matrix comprising:
        (i) from about 1.5% to about 5% of behenyl trimethyl ammonium chloride;
        (ii) from about 2% to about 8% of mixture of stearyl alcohol and cetyl alcohol compound; and
        (iii) an aqueous carrier;
wherein the composition is prepared by a method comprising the steps of:
    (a) mixing the first, second, and third silicones to form the pre-mixture of the silicone system; and
    (b) mixing the pre-mixture of the silicone system with the gel matrix.

* * * * *